(12) United States Patent
Omura et al.

(10) Patent No.: US 6,512,099 B2
(45) Date of Patent: Jan. 28, 2003

(54) ROSELIPIN DERIVATIVE

(75) Inventors: Satoshi Omura, Minato-ku (JP); Hiroshi Tomoda, Minato-ku (JP)

(73) Assignee: Kitasato Institute, Tokyo (FR)

( * ) Notice: Subject to any disclaimer, the term of this patent is extended or adjusted under 35 U.S.C. 154(b) by 0 days.

(21) Appl. No.: 10/096,942

(22) Filed: Mar. 14, 2002

(65) Prior Publication Data

US 2002/0193315 A1 Dec. 19, 2002

(30) Foreign Application Priority Data

Mar. 23, 2001 (JP) ........................ 2001-084565

(51) Int. Cl.$^7$ ................... C07G 11/00; C07G 3/00; C07H 15/00; C07H 17/00
(52) U.S. Cl. ............................ 536/4.1; 540/183
(58) Field of Search ................. 536/107, 4.1; 514/25; 435/822

(56) References Cited

PUBLICATIONS

The Journal of Antibiotics, Tabata et al., "Structure Elucidation of Roselipins, Inhibitors of Diacylglycerol Acyltransferase", vol. 52, No. 9, pp. 815–826, 09/99.

The Journal of Antibiotics, Tomoda et al., "Roselipins, Inhibitors of Diacylglycerol Acyltransferase, Produced by Gliocladium Roseum KF–1040", vol. 52, No. 8, pp. 689–694, 08/99.

Primary Examiner—James O. Wilson
Assistant Examiner—Ganapathy Krishnan
(74) Attorney, Agent, or Firm—Young & Thompson

(57) ABSTRACT

Roselipin derivatives which are represented by the following formula:

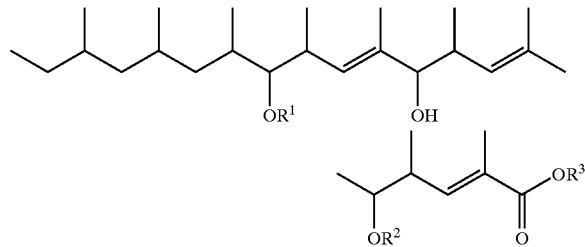

[wherein $R^1$ represents a hydrogen atom, mannose or acetylated mannose, $R^2$ represents a hydrogen atom or a methyl group, and $R^3$ represents a methyl group or a sugar alcohol], excluding a compound in which $R^1$ is mannose, $R^2$ is a hydrogen atom and $R^3$ is arabinitol (roselipin 1A or 1B) and a compound in which $R^1$ is acetylated mannose, $R^2$ is a hydrogen atom and $R^3$ is arabinitol (roselipin 2A or 2B), and which are useful for preventing and treating a disease of a human which is caused by accumulation of triacylglycerol can be obtained.

2 Claims, No Drawings

ROSELIPIN DERIVATIVE

BACKGROUND OF THE INVENTION (i) Field of the Invention

The present invention relates to a roselipin derivative having an inhibitory activity against diacylglycerol acyltransferase and useful for preventing and treating a disease of a human such as obesity or hyperlipidemia which is caused by accumulation of triacylglycerol.

(ii) Description of the Related Art

Heretofore, several antiobestic drugs and drugs for hyperlipidemia are known. A central anorectic reduces biosynthesis of lipids by suppressing an appetite. However, on the contrary, it may be detrimental to one's health since it reduces his/her appetite. For this reason, developments of novel antiobestic drug and drug for hyperlipidemia free from side effects have been desired.

SUMMARY OF THE INVENTION

In recent years, there is a tendency that along with an improvement in dietary habit, the number of patients suffering from obesity or hyperlipidemia which is caused by accumulation of triacylglycerol has been increasing. This presents a serious problem from the viewpoints of curative medicine and preventive medicine since these diseases cause or induce a variety of lesions. Illustrative examples of diseases which are supervened by obesity or hyperlipidemia caused by accumulation of triacylglycerol include arteriosclerosis, a fatty liver, high blood pressure and diabetes. There is a tendency that the number of patients suffering from these diseases is now increasing.

Obesity is a state of a body in which a deposit fat, especially triglyceride, is accumulated excessively and is caused by abnormal accumulation of fats in fat cells which is ascribable to an increase in synthesis of triacylglycerol. Triacylglycerolemia is also considered to induce lipoproteinemia containing a high level of triacylglycerol in blood due to an increase in synthesis of triacylglycerol in intestines or a liver. Therefore, a substance which inhibits diacylglycerol acyltransferase responsible for selective synthesis of triacylglycerol is expected to suppress accumulation of triacylglycerol and be effective at treating such diseases.

Under the above circumstances, provision of a substance having an inhibitory activity against diacylglycerol acyltransferase is useful for preventing and treating obesity and hyperlipidemia and a variety of adult diseases based on these diseases, as exemplified by arteriosclerosis, a fatty liver, high blood pressure and diabetes.

The present inventors have continuously made a variety of studies on metabolites produced by microorganisms and have newly found that substances having an inhibitory activity against diacylglycerol acyltransferase are produced in a culture of a KF-1040 strain separated from soil and have made an international application for the finding [PCT/JP98/00614(WO99/41265)]. This international application has become U.S. patent application Ser. No. 09/581,660. The present inventors have continued to make studies and succeeded in separating the substances having an inhibitory activity against diacylglycerol acyltransferase from the culture of a KF-1040-strain and purifying the substances. As a result, since the substances having the following chemical structures have heretofore been completely unknown, the substances in the present invention are named as roselipin 1A, roselipin 1B, roselipin 2A and roselipin 2B and named as roselipins as a whole (Tomoda et al., The Journal of Antibiotics, vol. 52, No. 8, pp. 689 to 694, August 1999 and Tabata et al., The Journal of Antibiotics, vol. 9, pp. 815 to 826, September 1999).

The chemical structure of the roselipin 1A is as follows.

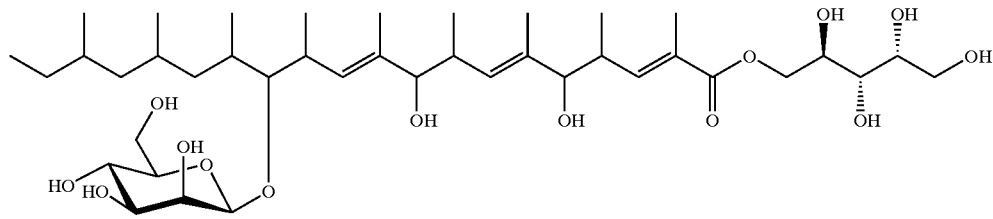

The chemical structure of the roselipin 1B is as follows.

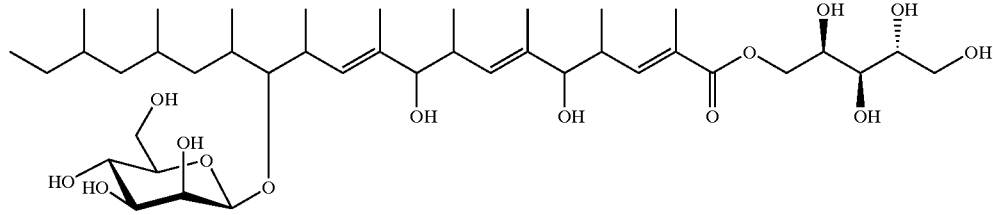

The chemical structure of the roselipin 2B is as follows.

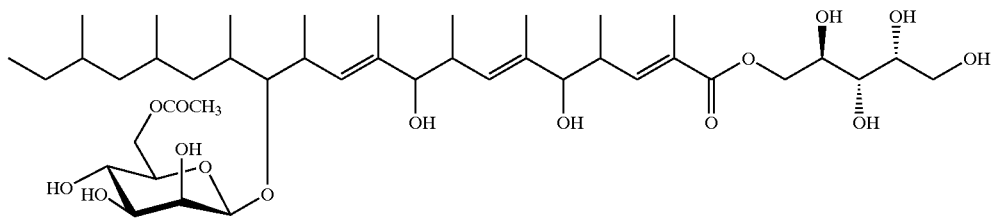

The chemical structure of the roselipin 2B is as follows.

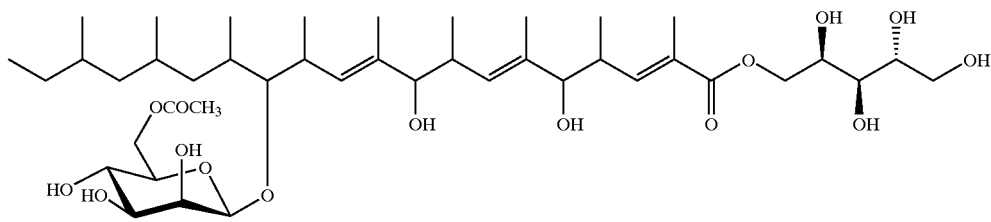

Consequently, the present inventors have succeeded in synthesizing a variety of roselipin derivatives for improving the diacylglycerol acyltransferase inhibiting activity (hereinafter referred to as "DGAT inhibiting activity") of the roselipins. The present invention has been completed based on the finding.

The present invention relates to roselipin derivatives represented by the following formula:

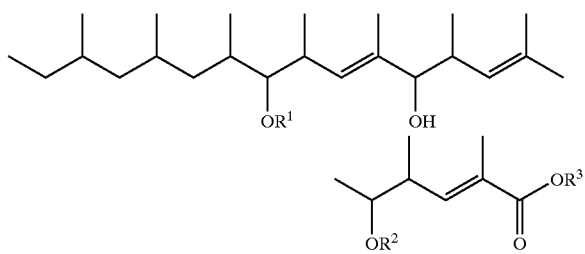

[wherein $R^1$ represents a hydrogen atom, mannose or acetylated mannose, $R^2$ represents a hydrogen atom or a methyl group, and $R^3$ represents a methyl group or a sugar alcohol]. The roselipin derivatives exclude a compound in which $R^1$ is mannose, $R^2$ is a hydrogen atom and $R^3$ is arabinitol (roselipin 1A or 1B) and a compound in which $R^1$ is acetylated mannose, $R^2$ is a hydrogen atom and $R^3$ is arabinitol (roselipin 2A or 2B).

Further, the present invention relates to derivatives which are compounds selected from the groups consisting of compounds whose groups $R^1$, $R^2$ and $R^3$ comprise a combination of the following substituents.

| compound | $R_1$ | $R_2$ | $R_3$ |
|---|---|---|---|
| roselipin R-3A | H | H | ![OH OH OH OH chain] |
| roselipin R-3B | H | H | ![OH OH OH OH chain] |

-continued

| compound | R₁ | R₂ | R₃ |
|---|---|---|---|
| roselipin R-4 | (sugar structure: cyclohexane ring with OH, OH, HO, HO, and -O- linkage) | H | $CH_3$ |
| roselipin R-5 | H | $CH_3$ | $CH_3$ |

The roselipin 1A, roselipin 1B, roselipin 2A and roselipin 2B which are starting materials of the roselipin derivatives of the present invention can be obtained as a product obtained by culturing Gliocladium sp. KF-1040 which is a microorganism disclosed in the aforementioned PCT/JP98/00614 (WO99,/41265). The strain has been domestically deposited with National Instituent Bioscience and Technology Agency of Industrial Science and Technology, which is located at 1–3, Higashi 1-chome, Tsukuba-shi, Ibaragi-ken, on Feb. 6, 1998 (Fermentation Research Institute No. P-16629) and then transferred to and internationally deposited with International Patent Organism Depository National Institute of Advanced Industrial Science and Technology, which is located at AIST Tsukuba Central 6, 1-1, Higashi 1-chome, Tsukuba-shi, Ibaraki-ken, Japan, zip. 305–8566, on Feb. 12, 1998 based on BUDAPEST TREATY ON THE INTERNATIONAL RECOGNITION OF THE DEPOSIT OF MICROORGANISMS FOR THE PURPOSE OF PATENT PROCEDURE (Depository No. FERM BP-6251). The above roselipins 1A, 1B, 2A and 2B are obtained in the following manner.

EXAMPLES

Next, purification of the roselipin 1A, roselipin 1B, roselipin 2A and roselipin 2B (may also be referred to as "roselipins 1A, 1B, 2A and 2B" hereinafter) which are starting materials in the present invention and purification of the roselipin R-3A compound, roselipin R-3B compound, roselipin R-4 compound and roselipin R-5 compound will be described in detail hereinafter.

Example 1

Purification of Roselipins 1A, 1B, 2A and 2B

As a seed culture for producing roselipins (roselipins 1A, 1B, 2A and 2B), 100 ml of seed medium [preservative slant medium (PDA) (3.9% potato dextrose agar medium) having Gliocladium sp. KF-1040 (FERM BP-6251) strain grown on 2% glucose, 0.2% yeast extract, 0.05% $MgSO_4 \cdot 7H_2O$, 0.5% polypeptone, 0.1% $KH_2PO_4$ and 0.1% agar (pH: 6.0)] was inoculated with an inoculating loop into a 500-ml Erlenmeyer flask and subjected to culture under shaking (at 210 rpm) at 27° C. for 5 hours to obtain a seed culture solution. Then, 200 ml of production culture (10% potato, 1.0% glucose and 50% sea water) was charged into a 1,000-ml Roux flask, and 4 ml of the above seed culture solution was then implanted on the production culture and left to be cultured at 27° C. for 15 days.

After 4.8 liters of the culture solution cultured for 15 days was treated with 9.0 liters of acetone, the resulting solution was filtered and concentrated under reduced pressure, and the remaining aqueous solution was then extracted from 9.0 liters of ethyl acetate. After dried over sodium sulfate anhydrous, the extract was filtered and concentrated under reduced pressure to give 2.20 g of brown, oily substance. This substrate was subjected to ODS column chromatography (Senshu SS 1020T, 50 g, Senshu Kagaku Shya) and eluted stepwise by use of 30%, 50%, 70% and 100% $CH_3CN$ (400 ml each), and 50 ml of each resulting eluate was collected. An aqueous solution left after the $17^{th}$ to $22^{nd}$ fractions containing roselipins were concentrated under reduced pressure was extracted from 300 ml of ethyl acetate. The extract was dried over sodium sulfate anhydrous, filtered and concentrated under reduced pressure to give 191 mg of yellow powdery substance.

This substance was further subjected to isolation and purification by means of HPLC [column: YMS pack D-ODS-AM (20×250 mm), mobile phase: 50% aq $CH_3CN$, detecting UV: 220 nm, flow rate: 6.0 ml/min]. As a result, roselipins 1A, 1B, 2A and 2B were eluted at 96 minutes, 100 minutes, 212 minutes and 224 minutes, respectively. However, the components A and B could not be separated from each other for the first time around.

Thus, after the material was subjected to the HPLC again under the same conditions as described above, an aqueous solution left after collected fractions were concentrated under reduced pressure was extracted from ethyl acetate to give 2.10 mg of white powdery roselipin 1A, 3.92 mg of white powdery roselipin 1B, 3.43 mg of colorless oily roselipin 2A, and 10.1 mg of colorless oily roselipin 2B. When the thus isolated and purified components were analyzed by means of HPLC [column: CAPCELL PAK UG (4.6×250 mm), mobile phase: 50% aq $CH_3CN$, detecting UV: 220 nm, flow rate: 0.7 ml/min], the roselipins 1A, 1B, 2A and 2B were eluted at 28 minutes, 29 minutes, 48 minutes and 49 minutes, respectively, and each had a purity of not lower than 95% according to their areas.

Example 2

Purification of Roselipin R-3A Compound 8.18 mg of the roselipin 1A obtained in Example 1 was suspended in 10 ml of 0.05M citric acid buffer solution (pH: 4.5) and 100 μl of 10 mg/ml of taurodeoxycholate sodium salt, 20 units of β-mannosidase (manufacture by SIGMA CO., LTD.) derived from a, snail were added thereto, and the resulting mixture was allowed to react at 37° C. under agitation. On the eighth day, 10 more units of the β-mannosidase (manufacture by SIGMA CO., LTD.) derived from a snail were further added, and the reaction was terminated on the $32^{nd}$ day from the start of the reaction. The reaction solution was separated by means of HPLC (YMC-Pack ODS-AM 20×250 mm, 80% $CH_3CN$, flow rate: 6 ml/min), and 3.20 mg of the compound on the title which was eluted at 34 minutes was isolated and purified.

The physical and chemical properties of the above isolated and purified roselipin R-3A compound are as follows.

(1) Appearance: colorless and oily
(2) Molecular Formula: $C_{34}H_{62}O_9$
(3) Molecular Weight: 614
(4) FAB-MS (m/z)
Positive: 615 $[M+H]^+$: 637 $[M+Na]^+$
Negative: 613 $[M-H]^-$
(5) HRFAB-MS (m/z), $C_{34}H_{62}O_9$ Na $[M+Na]^+$
Calculated Value: 637.4291
Measured Value: 637.4283
(6) Specific Rotation $[\alpha]_D^{24}+18°$ (c=0.1, in methanol)
(7) Ultraviolet Absorption Spectrum: λ max=202 nm ($CH_3OH$, log ε=19,000) and 221 nm ($CH_3OH$, log ε=14, 100)
(8) Infrared Absorption Spectrum (KBr): ν max=3,421, 2,960, 2,926, 2,873, 2,854, 1,714, 1,647, 1,583, 1,456, 1,377, 1,271, 1,227, 1,078 and 1,018 $cm^{-1}$
(9) Solubility in Solvents: soluble in $CH_3OH$, $CHCl_3$, $CH_3CN$, acetone, $C_2H_5OH$ and ethyl acetate and insoluble in $H_2O$ and n-hexane
(10) Color Reaction: positive in a 50% $H_2SO_4$ reaction and negative in a ninhydrine reaction
(11) Chemical Shifts of $^{13}C$-Nuclear Magnetic Resonance Spectrum (NMR) Measured by Use of XL-400 (manufactured by BARIAN CO., LTD.) and Heavy Methanol as a Solvent: 170.05, 128.81, 147.57, 38.02, 83.71, 137.14, 134.30, 37.08, 84.33, 134.79, 134.69, 36.20, 87.31, 34.27, 43.93, 28.85, 46.04, 32.91, 29.86, 11.53, 12.88, 16.81, 11.36, 17.82, 11.32, 18.63, 15.56, 21.34, 20.73, 67.88, 70.63, 71.93, 71.64, 64.80
(12) Chemical Shifts of $^1H$-Proton Nuclear Magnetic Resonance Spectrum (NMR) Measured by Use of XL-400 (manufactured by BARIAN CO., LTD.) and Heavy Methanol as a Solvent, Integrals, Coupling Patterns and Coupling Constants: 6.80 (1H, dd, J=10.0, 1.5 Hz), 2.73 (1H, m), 3.82 (1H, d, J=8.5 Hz), 5.33 (1H, dd, J=9.0, 1.0, Hz), 2.62 (1H, m), 3.72 (1H, d, J=9.5 Hz), 5.56 (1H, dd, J=9.5, 1.0 Hz), 2.75 (1H, m), 3.49 (1H, dd, J=7.0, 3.5 Hz), 1.87 (1H, m), 0.95 (1H, m), 1.37 (1H, m), 1.62 (1H, m), 0.88 (1H, m), 1.24 (1H, m), 1.45 (1H, m), 1.08 (1H, m), 1.42 (1H, m), 0.89 (3H, t, J=7.0 Hz), 1.90 (3H, d, J=1.5 Hz), 0.86 (3H, d, J=7.0 Hz), 1.68 (3H, d, J=1.0 Hz), 0.78 (3H, d, J=7.0 Hz), 1.64 (3H, d, J=1.0 Hz), 0.99 (3H, d, J=7.0 Hz), 0.94 (3H, d, J=7.0 Hz), 0.90 (3H, d, J=6.5 Hz), 0.90 (3H, d, J=6.5 Hz), 4.25 (1H, dd, J=12.0, 6.5 Hz), 4.41 (1H, dd, J=12.0, 3.0 Hz), 3.94 (1H, ddd, J=9.0, 6.5, 3.0 Hz), 3.58 (1H, dd, J=9.0, 2.0 Hz), 3.92 (1H, ddd, J=6.5, 6.5, 2.0 Hz), 3.65 (2H, ddd, J=7.0, 6.5, 6.5 Hz)

As described in detail above, as a result of studying the physical and chemical properties and spectra data of the roselipin R-3A compound, it was determined that the roselipin R-3A compound had the following chemical structure.

salt, 10 units of β-mannosidase (manufacture by SIGMA CO., LTD.) derived from a: snail were added thereto, and the resulting mixture was allowed to react at 37° C. under agitation. On the tenth day, 5 more units of the β-mannosidase (manufacture by SIGMA CO., LTD.) derived from a snail were further added, and the reaction was terminated on the $31^{st}$ day from the start of the reaction. The reaction solution was separated by means of HPLC (YMC-Pack ODS-AM 20×250 mm, 80% $CH_3CN$, flow rate: 6 ml/min), and 1.01 mg of the compound on the title which was eluted at 34.5 minutes was isolated and purified.

The physical and chemical properties of the above isolated and purified roselipin R-3B compound are as follows.
(1) Appearance: colorless and oily
(2) Molecular Formula: $C_{34}H_{62}O_9$
(3) Molecular Weight: 614
(4) FAB-MS (m/z)
Positive: 615 $[M+H]^+$: 637 $[M+Na]^+$
Negative: 613 $[M-H]^-$
(5) HRFAB-MS (m/z), $C_{34}H_{62}O_9$ Na $[M+Na]^+$
Calculated Value: 637.4291
Measured Value: 637.4273
(6) Specific Rotation $[\alpha]_D^{24}+10°$ (c=0.054, in methanol)
(7) Ultraviolet Absorption Spectrum: λ max=202 nm ($CH_3OH$, log ε=30,100) and 219 nm ($CH_3OH$, log ε=22, 700)
(8) Infrared Absorption Spectrum (KBr): ν max=3,430, 2,960, 2,929, 2,873, 2,854, 1,701, 1,632, 1,583, 1,458, 1,385, 1,273, 1,228, 1,042 and 1,018 $cm^{-1}$
(9) Solubility in Solvents: soluble in $CH_3OH$, $CHCl_3$, $CH_3CN$, acetone, $C_2H_5OH$ and ethyl acetate and insoluble in $H_2O$ and n-hexane
(10) Color Reaction: positive in a 50% $H_2SO_4$ reaction and negative in a ninhydrine reaction
(11) Chemical Shifts of $^{13}C$-Nuclear Magnetic Resonance Spectrum (NMR) Measured by Use of XL-400 (manufactured by BARIAN CO., LTD.) and Heavy Methanol as a Solvent: 169.8, 128.73, 147.71, 38.07, 83.72, 137.20, 134.30, 37.12, 84.31, 134.84, 134.67, 36.24, 87.33, 34.29, 43.97, 28.90, 46.07, 32.94, 29.89, 11.52, 12.87, 16.82, 11.36, 17.82, 11.36, 18.63, 15.58, 21.35, 20.73, 67.16, 69.38, 72.30, 72.71, 65.03
(12) Chemical Shifts of $^1H$-Proton Nuclear Magnetic Resonance Spectrum (NMR) Measured by Use of XL-400 (manufactured by BARIAN CO., LTD.) and Heavy Methanol as a Solvent, Integrals, Coupling Patterns and Coupling Constants: 6.78 (1H, dd, J=10.0, 1.5 Hz), 2.75 (1H, m), 3.82 (1H, d, J=9.0 Hz), 5.33 (1H, dd, J=9.0, 1.0 Hz), 2.63 (1H, m), 3.72 (1H, d, J=9.5 Hz), 5.57 (1H, dd, J=9.5, 1.5 Hz), 2.76 (1H, m), 3.49 (1H, dd, J=7.0, 3.5 Hz), 1.87 (1H, m), 1.02 (1H, m), 1.42 (1H, m), 1.62 (1H, m), 0.94 (1H, m), 1.27 (1H,

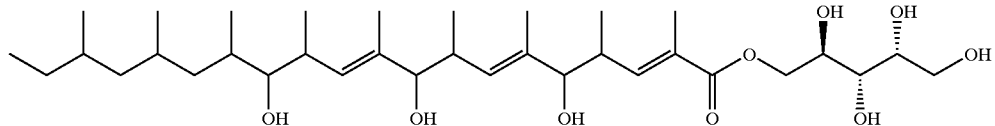

Example 3

Purification of Roselipin R-3B Compound 3.00 mg of the roselipin 1B obtained in Example 1 was suspended in 5 ml of 0.05M citric acid buffer solution (pH: 4.5) and 50 μl of 10 mg/ml of taurodeoxycholate sodium m), 1.45 (1H, m), 1.22 (1H, m), 1.45 (1H, m), 0.89 (3H, t, J=6.5 Hz), 1.89 (3H, d, J=1.5 Hz), 0.85 (3H, d, J=7.0 Hz), 1.67 (3H, d, J=1.0 Hz), 0.78 (3H, d, J=7.0 Hz), 1.64 (3H, d, J=1.5 Hz), 0.99 (3H, d, J=7.0 Hz), 0.95 (3H, d, J=7.0 Hz), 0.90 (3H, d, J=7.0 Hz), 0.90 (3H, d, J=7.0 Hz), 4.20 (1H, dd, J=11.0, 5.5 Hz), 4.27 (1H, dd, J=11.0, 7.0 Hz), 4.14 (1H, ddd, J=7.0, 5.5, 2.0 Hz), 3.53 (1H, dd, J=8.0, 2.0 Hz), 3.73 (1H, ddd, J=8.0, 6.0, 3.5 Hz), 3.64 (1H, dd, J=11.0, 6.0 Hz), 3.81 (1H, dd, J=11.0, 3.5 Hz)

As described in detail above, as a result of studying the physical and chemical properties and spectra data of the roselipin R-3B compound, it was determined that the roselipin R-3B compound had the following chemical structure.

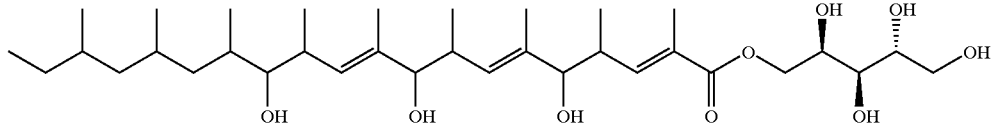

Example 4

Purification of Roselipin R-4 Compound 50 mg of a mixture of the roselipins 1A and 1B obtained in Example 1 was dissolved in 1 ml of methanol. After the mixture was allowed to react at room temperature for two days, the reaction solution was separated by means of HPLC (YMC-Pack ODS-AM 20×250 mm, 80% $CH_3CN$, flow rate: 6 ml/min), and 25.5 mg of the compound on the title which was eluted at 64 minutes was isolated and purified.

The physical and chemical properties of the above isolated and purified roselipin R-4 compound are as follows.

(1) Appearance: colorless and oily
(2) Molecular Formula: $C_{36}H_{64}O_{10}$
(3) Molecular Weight: 656
(4) FAB-MS (m/z)
Positive: 679 [M+Na]$^+$
Negative: 655 [M+H]$^-$ 34.26, 43.95, 28.88, 46.04, 32.93, 29.88, 11.53, 12.84, 16.82, 11.34, 17.81, 11.31, 18.61, 15.59, 21.36, 20.74, 52.20, 102.64, 72.69, 75.67, 68.55, 78.25, 62.95

(12) Chemical Shifts of $^1$H-Proton Nuclear Magnetic Resonance Spectrum (NMR) Measured by Use of XL-400 (manufactured by BARIAN CO., LTD.) and Heavy Methanol as a Solvent, Integrals, Coupling Patterns and Coupling Constants: 6.73 (1H, dd, J=10.0, 1.5 Hz), 2.73 (1H, m), 3.80 (1H, d, J=8.5 Hz), 5.32 (1H, dd, J=9.5, 1.0 Hz), 2.62 (1H, m), 3.71 (1H, d, J=9.5 Hz), 5.56 (1H, dd, J=9.5, 1.0 Hz), 2.75 (1H, m), 3.49 (1H, dd, J=6.5, 3.5 Hz), 1.87 (1H, m), 1.00 (1H, m), 1.39 (1H, m), 1.62 (1H, m), 0.91 (1H, m), 1.26 (1H, m), 1.45 (1H, m), 1.08 (1H, m), 1.42 (1H, m), 0.89 (3H, t, J=7.0 Hz), 1.87 (3H, d, J=1.5 Hz), 0.84 (3H, d, J=7.0 Hz), 1.67 (3H, d, J=1.0 Hz), 0.78 (3H, d, J=7.0 Hz), 1.64 (3H, d, J=1.0 Hz), 0.99 (3H, d, J=7.0 Hz), 0.95 (3H, d, J=7.0 Hz), 0.90 (3H, d, J=6.5 Hz), 0.90 (3H, d, J=6.5 Hz), 3.73 (3H, s), 4.49 (1H, bs), 3.90 (1H, d, J=3.0 Hz), 3.38 (1H, dd, J=9.5, 3.0 Hz), 3.57 (1H, dd, J=9.5, 9.5 Hz), 3.16 (1H, ddd, J=9.5, 5.0, 2.5 Hz), 3.76 (1H, dd, J=11.5, 5.0 Hz), 3.89 (1H, dd, J=11.5, 2.5 Hz)

As described in detail above, as a result of studying the physical and chemical properties and spectra data of the roselipin R-4 compound, it was determined that the roselipin R-4 compound had the following chemical structure.

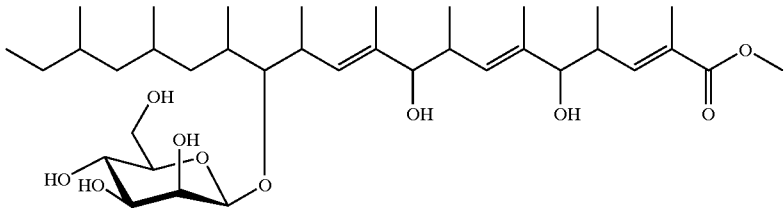

(5) HRFAB-MS (m/z), $C_{36}H_{64}O_{10}Na$ [M+Na]$^+$
Calculated Value: 679.4397
Measured Value: 679.4391
(6) Specific Rotation $[\alpha]_D^{24}$+12° (c=0.1, in methanol)
(7) Ultraviolet Absorption Spectrum: λ max=202 nm ($CH_3OH$, log ε=17,700) and 221 nm ($CH_3OH$, log ε=13,300)
(8) Infrared Absorption Spectrum (KBr): ν max=3,430, 2,962, 2,926, 2,875, 1,714, 1,641, 1,458, 1,379, 1,269, 1,227, 1,124, 1,072 and 1,026 cm$^{-1}$
(9) Solubility in Solvents: soluble in $CH_3OH$, $CHCl_3$, $CH_3CN$, acetone, $C_2H_5OH$ and ethyl acetate and insoluble in $H_2O$ and n-hexane
(10) Color Reaction: positive in a 50% $H_2SO_4$ reaction and negative in a ninhydrine reaction
(11) Chemical Shifts of $^{13}$C-Nuclear Magnetic Resonance Spectrum (NMR) Measured by Use of XL-400 (manufactured by BARIAN CO., LTD.) and Heavy Methanol as a Solvent: 170.35, 128.55, 147.65, 38.03, 83.77, 137.20, 134.35, 37.12, 84.35, 134.84, 134.67, 36.23, 87.28,

Example 5

Purification of Roselipin R-5 Compound

After 20 mg of a mixture of the roselipins 1A, 1B, 2A and 2B obtained in Example 1 was reacted with 2N HCl MeOH at 80° C. for 12 hours, the reaction solution was separated by means of HPLC (YMC-Pack ODS-AM 20×250 mm, 100% $CH_3CN$, flow rate: 6 ml/min), and 1.38 mg of the compound on the title which was eluted at 59 minutes was isolated and purified.

The physical and chemical properties of the above isolated and purified roselipin R-5 compound are as follows.

(1) Appearance: colorless and oily
(2) Molecular Formula: $C_{31}H_{56}O_5$
(3) Molecular Weight: 508
(4) FAB-MS (m/z)
Positive: 531 [M+Na]$^+$
Negative: 507 [M+H]$^-$
(5) HRFAB-MS (m/z), $C_{31}H_{56}O_5Na$ [M+Na]$^+$ Calculated Value: 531.4025

Measured Value: 531.4030

(6) Specific Rotation $[\alpha]_D^{24}+14°$ (c=0.028, in methanol)

(7) Ultraviolet Absorption Spectrum: λ max=206 nm ($CH_3OH$, log ε=62,900) and 216 nm ($CH_3OH$, log ε=59,900)

(8) Infrared Absorption Spectrum (KBr): ν max=3,434, 2,962, 2,927, 2,873, 1,718, 1,655, 1,458, 1,377, 1,269, 1,234, 1,128, 1,099 and 1,028 $cm^{-1}$ (9) Solubility in Solvents: soluble in $CH_3OH$, $CHCl_3$, $CH_3CN$, acetone, $C_2H_5OH$ and ethyl acetate and insoluble in $H_2O$ and n-hexane

(10) Color Reaction: positive in a 50% $H_2SO_4$ reaction and negative in a ninhydrine reaction

(11) Chemical Shifts of $^{13}C$-Nuclear Magnetic Resonance Spectrum (NMR) Measured by Use of XL-400 (manufactured by BARIAN CO., LTD.) and Heavy Methanol as a Solvent: 170.35, 128.31, 147.63, 37.49, 93.51, 132.48, 136.40, 36.44, 78.73, 134.50, 128.86, 32.13, 80.00, 32.35, 44.12, 29.19, 46.17, 32.95, 29.76, 11.56, 12.80, 16.93, 10.91, 16.63, 20.49, 19.39, 15.54, 20.79, 21.03, 52.22, 56.72

(12) Chemical Shifts of $^1H$-Proton Nuclear Magnetic Resonance Spectrum (NMR) Measured by Use of XL-400 (manufactured by BARIAN CO., LTD.) and Heavy Methanol as a Solvent, Integrals, Coupling Patterns and Coupling Constants: 6.67 (1H, dd, J=10.0, 1.5 Hz), 2.72 (1H, m), 3.32 (1H, d, J=8.5 Hz), 5.63 (1H, dd, J=9.5, 1.5 Hz), 2.87 (1H, m), 3.87 (1H, brd, J=5.0 Hz), 5.47 (1H, dd, J=4.0, 1.0 Hz), 2.18 (1H, m), 3.20 (1H, dd, J=6.5, 5.0 Hz), 1.80 (1H, m), 1.02 (1H, m), 1.46 (1H, m), 1.62 (1H, m), 0.91 (1H, m), 1.26 (1H, m), 1.46 (1H, m), 1.08 (1H, m), 1.42 (1H, m), 0.89 (3H, t, J=7.0 Hz), 1.84 (3H, d, J=1.5 Hz), 0.85 (3H, d, J=7.0 Hz), 1.59 (3H, d, J=1.5 Hz), 0.99 (3H, d, J=7.0 Hz), 1.69 (3H, d, J=1.0 Hz), 0.97 (3H, d, J=7.0 Hz), 0.87 (3H, d, J=7.0 Hz), 0.89 (3H, dd, J=7.0 Hz), 0.87 (3H, d, J=7.0 Hz), 3.73 (3H, s), 3.15 (3H, s)

As described in detail above, as a result of studying the physical and chemical properties and spectra data of the roselipin R-5 compound, it was determined that the roselipin R-5 compound had the following chemical structure.

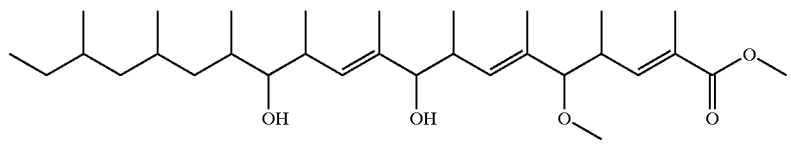

Next, the biological properties of the roselipin R-3A, R-3B, R-4 and R-5 compounds will be described in detail hereinafter.

(1) Inhibitory Activity against Diacylglycerol Acyltransferase Derived From Rat

A diacylglycerol acyltransferase activity was measured by means of a partially modified version of a method of Mayorek and Bar-Tana (Journal of Biological Chemistry, vol. 260, pp. 6,538 to 6,532, 1985).

That is, using a microsome fraction prepared from a rat liver as an enzyme source, 0.75 mM 1,2-dioleoyl-sn-glycerol and 30 µM [$1-^{14}C$]palmitoyl-CoA (0.02 µCi) were added to 175 mM tris-hydrochloric acid (HCl)(pH: 8.0) buffer containing 8 mM $MgCl_2$, 1 mg/ml bovine serum albumin and 2.5 mM diisopropyl fluorophosphonate to a total volume of 200 µL. The mixture was allowed to react at 23° C. for 15 minutes. After all lipids were extracted from a mixed solution of chloroform and methanol (mixing ratio=1:2), the lipids were separated by use of TLC (Silicagel 60 $CF_{254}$ and developing solvent containing petroleum ether, diethyl ether and acetic acid (80:20:1)). Thereafter, the radioactivity of a triacylglycerol fraction was measured by an RI radio scanner (manufactured by AMBIS CO., LTD.) to measure the diacylglycerol acyltransferase activity.

The concentrations of the roselipin R-3A, R-3B, R-4 and R-5 compounds which inhibited 50% of the diacylglycerol acyltransferase were measured. As a result, the roselipin R-3A, R-3B, R-4 and R-5 compounds were 60 µM, 33 µM, >762 µM and >984 µM, respectively.

(2) Inhibitory Activity against Production of Triacylglycerol in Human-Derived Cell (Raji Cell Derived From Human Burkitt Lymphoma)

An influence on production of triacylglycerol was examined in accordance with a method by TOMODA et al. (Journal of Biological Chemistry, vol. 266, pp. 4,212 to 4,219, 1991) by use of a human-derived cell (Raji cell derived from human Burkitt lymphoma).

200 µl of 2.7×10⁵ cells/ml of Raji cell solution [$1-^{14}C$] oleic acid (0.02 µCi) was allowed to react at 37° C. for 30 minutes. After all lipids were extracted from a mixed solution of chloroform and methanol (mixing ratio=1:2), a measurement was carried out by use of the same method as used for the inhibitory activity against diacylglycerol acyltransferase derived from a rat. The concentrations of the roselipin R-3A, R-3B, R-4 and R-5 compounds which inhibited 50% of production of triacylglycerol were measured. As a result, the roselipin R-3A, R-3B, R-4 and R-5 compounds were 11 µM, 10 µM, 200 µM and 250 µM, respectively.

The antibacterial activities of the roselipin derivatives of the present invention were measured in accordance with a method by Zhong et al. (Journal of Antibiotics, vol. 52, pp. 29 to 33, 1999).

Bacteria were cultured in a Muller-Hinton-agar culture medium (manufactured by Difco Co., Ltd.) at 37° C. for 24 hours, and mold and yeasts were cultured in a potato-dextrose-agar culture medium (manufactured by Difco Co., Ltd.) at 27° C. for 48 hours. A piece of circular filter paper (manufactured by ADVANTECH CO., LTD.) having a diameter of 6 mm was placed on each of the culture media, and the filter paper was impregnated with 10 µg of each of the roselipin derivatives to measure a growth inhibition circle for each test fungus. The results of the measurement are as follows.

| Test Fungus | Diameter of Inhibition Circle (mm) | | | |
| --- | --- | --- | --- | --- |
|  | R-3A | R-3B | R-4 | R5 |
| Bacillus subtilis KB27 (synthetic medium) | 10 | + | + | − |
| Bacillus subtilis KB27 (natural medium) | + | + | − | − |

-continued

| Test Fungus | Diameter of Inhibition Circle (mm) | | | |
|---|---|---|---|---|
| | R-3A | R-3B | R-4 | R5 |
| *Staphylococcus aureus* KB210 | − | − | − | − |
| *Micrococcus luteus* KB40 | − | − | + | − |
| *Mycobacterium smegmatis* KB42 | − | − | − | − |
| *Escherichia coli* KB176 | − | − | − | − |
| *Pseudomonau aeruginosa* KB105 | − | − | − | − |
| *Xanthomonas campestris* pv. oryzae | − | − | − | − |
| *Bacterioides fragilis* KB169 | − | − | − | − |
| *Acholeplasma laidlawii* KB174 | 10 | + | − | − |
| *Pyricularia oryzae* KB180 | − | − | 16 | − |
| *Aspergillus niger* KB103 | − | − | − | − |
| *Mucor racemosus* KF223 | 14 | − | 12 | − |
| *Candida albicans* KF1 | − | − | − | − |
| *Saccharomyces cerevisiae* KF26 | − | − | − | − |

As described above, the roselipin derivatives of the present invention exhibit an inhibitory activity against diacylglycerol acyltransferase. Therefore, they are useful for preventing and treating a disease of a human which is caused by accumulation of triacylglycerol.

What is claimed is:

1. A roselipin derivative represented by the following formula:

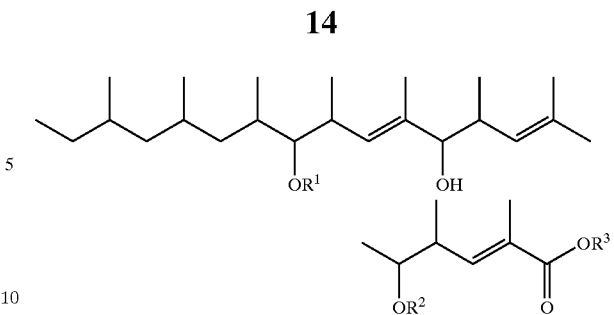

wherein $R^1$ represents a hydrogen atom, mannose or acetylated mannose, $R^2$ represents a hydrogen atom or a methyl group, and $R^3$ represents a methyl group or a sugar alcohol, excluding a compound in which $R^1$ is mannose, $R^2$ is a hydrogen atom and $R^3$ is arabinitol (roselipin 1A or 1B) simultaneously and a compound in which $R^1$ is acetylated mannose, $R^2$ is a hydrogen atom and $R^3$ is arabinitol (roselipin 2A or 2B) simultaneously.

2. The roselipin derivative according to claim 1, which is selected from the group consisting of compounds whose groups $R^1$, $R^2$ and $R^3$ comprise a combination of the following constituents:

| compound | $R^1$ | $R^2$ | $R^3$ |
|---|---|---|---|
| roselipin R-3A | H | H | (tetraol chain with OH, OH, OH, OH) |
| roselipin R-3B | H | H | (tetraol chain with OH, OH, OH, OH) |
| roselipin R-4 | (sugar with OH, OH, HO, HO, O) | H | CH₃; and |
| roselipin R-5 | H | CH₃ | CH₃.— |

* * * * *